US006245551B1

United States Patent
Lehman et al.

(10) Patent No.: US 6,245,551 B1
(45) Date of Patent: Jun. 12, 2001

(54) **STRAIN OF *BACILLUS PUMILUS* FOR CONTROLLING PLANT DISEASES CAUSED BY FUNGI**

(75) Inventors: Lori Jo Lehman, Vacaville; Randy Jay McCoy, Davis; Belinda Jane Messenger, Davis; Denise Carol Manker, Davis; Jimmy Ensio Orjala, Davis; Dorte Lindhard, Davis; Pamela Gail Marrone, Davis, all of CA (US)

(73) Assignee: AgraQuest, Inc., Davis, CA (US)

( * ) Notice: Subject to any disclaimer, the term of this patent is extended or adjusted under 35 U.S.C. 154(b) by 0 days.

(21) Appl. No.: 09/281,360

(22) Filed: Mar. 30, 1999

(51) Int. Cl.$^7$ ...................................................... C12N 1/20
(52) U.S. Cl. ........................................ 435/252.5; 424/93.46
(58) Field of Search ........................ 435/252.5; 424/93.46

(56) References Cited

U.S. PATENT DOCUMENTS

| | | |
|---|---|---|
| 4,250,170 | 2/1981 | Kawaguchi et al. . |
| 5,047,239 | 9/1991 | Pusey . |
| 5,049,379 | 9/1991 | Handelsman et al. . |
| 5,061,495 | 10/1991 | Rossall . |
| 5,344,647 | 9/1994 | Rossall . |
| 5,403,583 | 4/1995 | Liu et al. . |
| 5,597,565 | 1/1997 | Leifert et al. . |
| 5,780,080 | 7/1998 | Leifert et al. . |

FOREIGN PATENT DOCUMENTS

| | | |
|---|---|---|
| 293 482 A5 | 9/1991 | (DE) . |
| 1817875 A3 | 5/1995 | (SU) . |

OTHER PUBLICATIONS

B'Chir, M.M. and Belkadhi, M.S., "Nouvelles donnees sur les modifications histologiques induites par le complexe *Fusarium solani—Tylenchulus semipenetrans* au niveau des racines de portes–greffes de citrus" *Med. Fac. Landbouww. Rijksuniv. Gent* 51(3b):1295–1310 (1986) English Abstract & Translation.

B'Chir, M.M. and Namouchi, N. "Effet de *Bacillus pimulus* sur *Monacrosporium salinium*, un champignon Prédateur de nématodes" *Revue Nématol.* 11(2):263–266 (1988) English Abstract.

Baker et al., "Inhibitory effect of *Bacillus subtillis* on *Uromyces phaseoli* and on development of rust pustules on bean leaves" *Phytopathol.* 73:1148–1152 (1983).

Ferreira et al., "Biological control of *Eutypa lata* on grapevine by an antogonistic strain of *Bacillus subtilis*" *Phytopathology* 81:283–287 (1991).

Gokte, N. and Swarup, G. "On the Association of Bacteria with Larvae and Galls of *Anguina tritic.*" *Indian J. Nematol.* 18(2):313–318 (1988).

He et al., "Zwittermycin A. an antifungal and plant protection agent from *Bacillus cereus*" *Tetrahedron Lett.* 35(16):2499–2502 (1994).

Islam, K.Z. and Nandi, B., "Control of brown spot of rice by *Bacillus megaterium*" *J. Plant Dis. Protect.* 92(3):241–246 (1985).

Islam, K.Z. and Nandi, B., "Inhibition of some fungal pathogens of hose phylloplane by *Bacillus megaterium*" *J. Plant Dis. Protect.* 92(3):233–240 (1985).

Korzybski, T. et al., "Section C: Antibiotics isolated from the genus Bacillus (Bacillaceae)" In: Antibiotics—Origin, Nature and Properties, American Society for Microbiology, Washington, D.C. 1978, vol. III, pp. 1529–1661 (1978).

Leifert et al., "Antibiotic production and biocontrol activity by *Bacillus subtilis* CL27 and *Bacillus pumilus* CL45" *J. Appl. Bacteriol.* 78:97–108 (1995).

Loeffler, W. et al., "Antifungal Effects of Bacilysin and Fengymycin from *Bacillus subtilis* F–29–3. A Comparison with Activities of Other Bacillus Antibiotics" *J. Phytopathol.* 115:204–213 (1986).

McInroy, J.A. and Kloepper, J.W., "Survey of indigenous bacterial endophytes from cotton and sweet corn" Plant and Soil 173(2):337–342 (1995).

McKeen et al., "Production and partial characterization of antifungal substances antagonistic to *Monilinia fructicola* from *Bacillus subtilis*" *Phytopathology* 76:136–139 (1986).

Milner et al., "Production of Kanosamine by *Bacillus cereus* UW85" *Appl. Environ. Microb.* 62:3061–3065 (1996).

Osburn et al., "Effect of *Bacillus cereus* UW85 on the yield of soybean at two field sites in Wisconsin" *Am. Phytopathol. Soc.* 79(6):551–556 (1995).

Pusey et al., "Pilot tests for commercial production and application of *Bacillus subtilis* (B–3) for postharvest control of peach brown rot" *Plant Dis.* 72:622–626 (1988).

Schwinn et al., "Control with Chemicals" in: Advances in Plant Pathology: Phytophthora Infestans, The Cause of Late Blight of Potato, vol. 7, Academic Press, San Diego, CA, p. 244 (1994).

Sholberg et al., "Biocontrol of postharvest diseases of apple using Bacillus spp. isolated from stored apples" *Can. J. Microbiol.* 41:247–252 (1995).

(List continued on next page.)

*Primary Examiner*—Irene Marx
(74) *Attorney, Agent, or Firm*—Antoinette F. Konski; Baker & McKenzie

(57) ABSTRACT

A novel antibiotic-producing Bacillus sp. is provided that exhibits antifungal activity only on certain specific plant pathogens and no antibacterial activity is provided by this invention as well as a biologically pure culture of a strain having all the identifying characteristics of this strain. Also provided is a method of treating or protecting plants, fruit and roots from fungal infections by applying an effective amount of these strains, supernatants produced by these strains or a metabolite isolated from these strains.

4 Claims, No Drawings

OTHER PUBLICATIONS

Singh, V. and Deverall, B.J., "*Bacillus subtilis* as a control agent against fungal pathogens of citrus fruit" *Trans. Br. Mycol. Soc.* 83:487–490 (1984).

Slabospitskaya, A.T. and Krymovskaya, S.S., "Chitinases of Aerobic Spore–Forming Bacteria Isolated from Different Ecological Sources" *Mikrobiol. Zh. (Kiev)* 54(6):16–22 (1992) Abstract in English.

Stabb et al., "Zwittermycin A–producing strains of *Bacillus cereus* from diverse soils" *Appl. Environ. Microbiol.* 60:4404–4412 (1994).

Swinburne et al., "Production of antibiotics by *Bacillus subtilis* and their effect on fungal colonists of apple leaf scars" *Trans. Brit. Mycol. Soc.* 65:211–217 (1975).

Tsuno et al., "3,3'–Nectrehalosadiamine (BMY–28251), A New Aminosugar Antibiotic " *J. Antibiotics* XXXIX(7):1001–1003 (Jul. 1986).

Cook, C.G. et al., "Effect of Treatment With Bacillus Species on Cotton Root Traits, Yield, and Phymatotrichum Root Rot" *Beltwide Cotton Production Research Conferences*, 1987 Proceedings, Jan. 4–8, 1987, Dallas, Texas, pp. 43–45 (1987).

US 6,245,551 B1

STRAIN OF BACILLUS PUMILUS FOR CONTROLLING PLANT DISEASES CAUSED BY FUNGI

FIELD OF THE INVENTION

The present invention is in the field of biopesticides. More particularly, this invention relates to the finding that a novel strain of *Bacillus pumilus*, NRRL accession number B-30087, can inhibit a broad range of fungal plant diseases in vivo. The invention also relates to fungicidal compositions comprising this novel Bacillus strain and the antibiotics and metabolites produced by this strain either alone, or in combination with other chemical and biological pesticides.

BACKGROUND

For a number of years, it has been known that various microorganisms exhibit biological activity so as to be useful to control plant diseases. Although progress has been made in the field of identifying and developing biological pesticides for controlling various plant diseases of agronomic and horticultural importance, most of the pesticides in use are still synthetic compounds. Many of these chemical fungicides are classified as carcinogens by the Environmental Protection Agency (EPA), are toxic to wildlife and other non-target species. In addition, pathogens may develop resistance to chemical pesticides (see, e.g., Schwinn et al., in: Advances In Plant Pathology: *Phytophthora Infestans*, The Cause of Late Blight of Potato, p. 244, Academic Press, San Diego, Calif., 1991).

Biological control offers an attractive alternative to synthetic chemical fungicides. Biopesticides (living organisms and the naturally produced compounds produced by these organisms) can be safer, more biodegradable, and less expensive to develop.

Bacilli are known to produce antifungal and antibacterial secondary metabolites (Korzybski et al. (1978) "Section C: Antibiotics isolated from the genus Bacillus (Bacillaceae)" in: *Antibiotics-Origin, Nature and Properties*, American Society for Microbiology, Washington, DC (1978) Vol III.) and by Berdy (CRC Handbook of Antibiotic Compounds, Vols. I–XIV, (CRC Press, Inc., Boca Raton, Fla. 1980–87). Compounds known to be produced by *B. pumilis* include micrococcin P, pumilin, and tetain.

Kawaguchi et al. 1981 (U.S. Pat. No. 4,250,170) isolated a novel water soluble antibiotic from Bacillus with activity against a broad range of gram positive and gram negative bacteria. Stabb et al. (1994) *Applied Environ. Microbiol.* 60:4404–4412 have identified certain Bacillus spp. (Bacillus spp. includes *B. subtilis, B. cereus, B. mycoides, B. thuringiensis*) strains that exhibit antifingal activity. These strains have been shown to produce zwittermicin-A and/or kanosamine (Milner et al., (1996) *Appl. Environ. Microb.* 62:3061–3066), two antibiotic agents that are effective against the soil borne disease damping off, caused by *Phytophthora medicaginis, P. nicotianae, P. aphanidermatum* or *Sclerotinia minor* (See Stabb et al., supra). Zwittermicin-A is a water soluble, acid stable linear aminopolyol molecule (see, He et al, (1994) *Tetrahedron Lett.* 35(16):2499–2502) with broad spectrum activity against many fungal and bacterial plant pathogens. Kanosamine (Milner et al., 1996) also inhibits a broad range of fungal plant pathogens and a few bacterial species.

U.S. Pat. No. 5,049,379 to Handelsman et al. describes how Zwittermicin-A producing *B. cereus* control damping off in alfalfa and soybeans. When the seed was coated with *B. cereus* ATCC 53522, the pathogenic activity of root rot fungus was inhibited. Similarly, application of spore-based formulations of certain *B. cereus* strains to soybean seeds or the soil surrounding the seeds has been shown to improve soybean yield at field sites. (See, Osburne et al. (1995) *Am. Phytopathol. Soc.* 79(6):551–556). Methods of applying biopesticides are well known in the art and include, for example, wettable powders, dry flowables, microencapsulation, and liquid formulations of the microbe, whole broth or antibiotic fractions from suitable cultures. (See e.g., U.S. Pat. No. 5,061,495 to Rossall or U.S. Pat. No. 5,049,379 to Handelsman).

Tsuno et al. (Takashi Tsuno, Chiharo Ikeda, Kei-ichi Numata, Koju Tomita, Masataka Konishi and Hiroshi Kawaguchi (1986) *J. Antibiotics* XXXIX(7):1001–1003) report on a new amino sugar antibiotic from *B. pumilus* with activity against a broad range of bacteria in vitro.

Leifert et al., *J. Appl Bacteriol.* 78:97–108 (1995), reported the production of anti-Botrytis and anti-Alternaria antibiotics by two Bacillus strains, *B. subtilis* CL27 and *B. pumilis* CL 45. The whole broth and cell-free filtrates were active against Botrytis and Alternaria in in vitro tests and were active against Botrytis in in vivo small plant tests on Astilbe. Leifert et al. (1997) U.S. Pat. No. 5,597,565 disclose *B. subtilis, B. pumilis*, and *B. polymyxa* that are particularly effective at inhibiting post harvest disease causing fungi, *Alternaria brassicicola* and *Botrytis cinerea*. They also disclose the presence of antibiotics produced in the cell-free culture filtrate and their activity at different pH values, but they do not identify these compounds. The compounds from *B. subtilis* lose activity at low pH, while the activity from the *B. pumilus* extracts occurs only at pH values below 5.6. Leifert et al. (1998) U.S. Pat. No. 5,780,080 discloses cabbages that can be treated with *B subtilis, B pumilis*, and *B. polymyxa* strains to inhibit *Alternaria brassicicola* and *Botrytis cinerea*

Loeffler et al. (1986) J. Phytopathology 115:204–213, disclose *B. subtilis, B. pumilus, B. licheniformis*, and *B. coagulans* strains that produce various antibiotics with antifungal and antibacterial activity. *B. pumilus* produced bacilysin and iturin A. Bacilysin is a very small compound with a molecular weight of 270, that inhibits only yeast. The iturins, which are soluble in polar solvents, have broad antifungal and antibacterial activity.

Rossall (1994) U.S. Pat. No. 5,344,647 discloses *Bacillus subtilis* strains with broad anti-fungal activity. Rossall's (1991) U.S. Pat. No. 5,061,495 provides a novel antibiotic from *B. subtilis* that is 63,500 Dalton, precipitates at a pH below 5 and has activity against gram positive bacteria and fungi (Botrytis and Erysiphe). Sholberg et al. (1995) *Can. J Microbiol.* 41:247–252, Swinburne et al. (1975) *Trans. Brit. Mycol. Soc.* 65:211–217, Singh and Deverall, (1984) *Trans. Br. Mycol. Soc.* 83:487–490, Ferreira et al. (1991) *Phytopathology* 81:283–287 and Baker et al. (1983) *Phytopathology* 73:1148–1152. All disclose the use of Bacillus spp. and *Bacillus subtilis* as biocontrol agents of fungal plant pathogens. Pusey et al. (1988) *Plant Dis.* 72:622–626, Pusey and Robins (U.S. Pat. No. 5,047,239), and McKeen et al. (1986) *Phytopathology* 76:136–139 disclose control of post harvest fruit rot using *B. subtilis*. McKeen et al., supra, have shown that antibiotics similar to the low molecular weight iturin cyclic polypeptides contribute to this fungicidal activity of *B. subtilis*.

Liu et al. (1995) U.S. Pat. No. 5,403,583 disclose a Bacillus sp., ATCC 55000 and a method to control the fungal plant pathogen, *Rhizoctonia solani*. Islam and Nandi (1985)

J. *Plant Dis. Protect.* 92(3):241–246, disclose a Bacillus sp. with antagonism to *Drechslera oryzae*, the causal agent of rice brown spot. The same authors, Islam and Nandi (1985) *J. Plant Dis. Protect.* 92(3):233–240, also disclose in-vitro antagonism of Bacillus sp. against *Drechslera oryzae, Alternaria alternata* and *Fusarium roseum*. They discuss three components in the culture filtrate. The most active antibiotic was highly soluble in water and methanol with a UV peak at 255 nm and a shoulder at 260 mn, that proved to be a polyoxin-like lipopeptide. Cook (1987) *Proceedings Beltwide Cotton Production—Mechanization Research Conference, Cotton Council*, Memphis, pp. 43–45 discloses the use of a suspension of Bacillus sp. to reduce the number of cotton plants killed by *Phymatotrichum omnivorum*, a cause of cotton root rot.

B'Chir and Namouchi (1988) (*Revue Nematologique* 11(2):263–266) report on a *Bacillus pumilus* that stimulates nematode trapping fungi to increase their ability to trap nematodes. B'Chir and Belkadhi (1986) (*Med. Fac. Landbouww. Rijksuniv. Gent 51/3b*:1295–1310) discuss the cellular interactions of a fungus (Fusarium) and nematodes that cause infection in citrus. The fungus is associated with *B. pumilis* (they occur together) and when the nematode is also there, the fungus is more severe. *B. pumilus* appears to be providing food for the nematodes. Gokte and Swarup (1988) (*Indian J. Nematol.* 18(2):313–318) report on *B. pumilus* that are nematicidal, but they do not report any antifungal activity. Slabospitskaya et al. (1992) (*Mikrobiol Zh (Kiev)* 54(6):16–22) compare many different Bacillus, including *B. pumilus* for their ability to produce chitinases, but they report no activity on plant pathogens. The *B. pumilus* produce the lowest chitinase levels. McInroy et al. (1995) *Plant and Soil* 173(2):337–342, did a survey of the many types of bacteria, including many Bacillus and *B. pumilus* that are endophytes within plant stems and roots. However, they show no evidence that these endophytic strains are antifungal. Chernin et al. (1995) *Molecular Genetics*, found a *Bacillus pumilus* that has a wide spectrum of activity against bacteria (e.g., Xanthomonas, Pseudomonas, Erwinia) and fungi that cause plant disease. Fey et al (1991) *Akad Landwirts Kart*, report on *B. pumilus* strains that provide seed potatoes some protection from *Rhizoctonia solani*.

DISCLOSURE OF THE INVENTION

A novel antibiotic-producing Bacillus sp. is provided that exhibits antifungal activity only on certain specific plant pathogens and no antibacterial activity. Also provided is a method of treating or protecting plants, fruit and roots from fungal infections comprising the step of applying an effective amount of an antibiotic-producing Bacillus sp. The antibiotic-producing Bacillus sp. can be provided as a suspension in a whole broth culture or as an antibiotic-containing supernatant obtained from a whole broth culture of an antibiotic-producing Bacillus sp. Also provided is a novel water-soluble antibiotic that exhibits specific antifungal activity and no antibacterial activity.

MODES FOR CARRYING OUT THE INVENTION

The present invention provides a biologically pure culture of a strain having all the identifying characteristics of a novel strain of Bacillus sp. or mutants thereof with antifungal activity only on specific plant pathogens such as rusts, powdery mildews and downy mildews. This novel strain is deposited with the NRRL on Jan. 14, 1999 under the provisions of the Budapest Treaty on the International Recognition of the Deposit of Microorganisms for the Purpose of Patent Procedure under Accession No. B-30087. The invention also includes methods of preventing and treating fungal diseases in plants, including plant roots, using such bacterial strains or antibiotic-containing supernatants or pure antibiotics obtained from such bacterial strains. The invention also includes a water soluble antifungal antibiotic with a molecular weight of less than 10,000 Dalton, slightly heat labile, positively charged, and an HPLC peak with UV absorbance at a maximum of 280 nm and a shoulder at 230 nm.

Definitions

As used in the specification and claims, the singular form "a", "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "isolated" is used interchangeably with "biologically pure" and means separated from constituents, cellular and otherwise, in which the strain or metabolite are normally associated with in nature.

As used herein, "biological control" is defined as control of a pathogen or insect by the use of a second organism. Known mechanisms of biological control include enteric bacteria that control root rot by out-competing fungi for space on the surface of the root. Bacterial toxins, such as antibiotics, have been used to control pathogens. The toxin can be isolated and applied directly to the plant or the bacterial species may administered so it produces the toxin in situ.

The term "fungus" or "fungi" includes a wide variety of nucleated spore-bearing organisms that are devoid of chlorophyll. Examples of fungi include yeast, molds, mildews, rusts, and mushrooms.

The term "bacteria" includes any prokaryotic organism that does not have a distinct nucleus.

"Fungicidal" means the ability of a substance to increase mortality or inhibit the growth rate of fungi.

"Antibiotic" includes any substance that is able to kill or inhibit a microorganism. Antibiotics may be produced by a microorganism or by a synthetic process or semisynthetic process. The term, therefore, includes a substance that inhibits or kills fungi for example, zwittermicin-A or kanosamine.

"Antifungal" includes any substance that is able to kill or inhibit the growth of fungi.

The term "culturing" refers to the propagation of organisms on or in media of various kinds.

"Whole broth culture" refers to a liquid culture containing both cells and media.

"Supernatant" refers to the liquid broth remaining when cells grown in broth are removed by centrifugation, filtration, sedimentation, or other means well known in the art.

An "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the fungal or bacterial disease states.

"Positive control" means a compound known to have pesticidal activity. "Positive controls" include, but are not limited to, commercially available chemical pesticides. The term "negative control" means a compound known not to have pesticidal activity. Examples of negative controls are water or ethyl acetate.

The term "solvent" includes any liquid that holds another substance in solution. "Solvent extractable" refers to any compound that dissolves in a solvent and which then may be isolated from the solvent. Examples of solvents include, but are not limited to, organic solvents like ethyl acetate.

The term "metabolite" refers to any compound, substance or byproduct of a fermentation of a microorganism that has pesticidal activity. Antibiotic as defined above is a metabolite specifically active against a microorganism.

A "composition" is intended to mean a combination of active agent and another compound or composition, inert (for example, a detectable agent or label) or active, such as an adjuvant.

We describe a biologically pure culture of a strain having all the identifying characteristics of a novel antibiotic-producing strain of Bacillus sp. NRRL No. B-30087, and mutants thereof, that have antifungal activity only on specific plant pathogens and no antibacterial activity. In one aspect, the strain is *Bacillus pumilis* deposited under NRRL No. B-30087, and mutants of the strain.

In other aspects, the strain is a variant of NRRL No. B-30087 which has all the identifying characteristics (as provided below) of NRRL No. B-30087. A variant may also be identified as having a genome that hybridizes under conditions of high stringency to the genome of NRRL No. B-30087. "Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency." In general, a low stringency hybridization reaction is carried out at about 40° C. in 10× SSC or a solution of equivalent ionic strength/temperature. A moderate stringency hybridization is typically performed at about 50° C. in 6× SSC, and a high stringency hybridization reaction is generally performed at about 60° C. in 1× SSC.

A variant of NRRL No. B-30087 may also be defined as a stain having a genomic sequence that is greater than 85%, more preferably greater than 90% or more preferably greater than 95% sequence identity to the genome of NRRL No. B-30087. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignent and the percent homology or sequence identity can be determined using software programs known in the art, for example those described in Current Protocols In Molecular Biology (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

This invention further provides the supernatants obtained from the above noted cultures. The supernatant may be obtained by methods well known in the art including: centrifugation; filtration; sedimentation; and the like.

In another aspect, the invention encompasses an isolated metabolite that is a water-soluble antifungal antibiotic. The metabolite is isolated from the strains of this invention and described above. It has the characteristics of being less than 10,000 Dalton, UV absorption peak at 280 nm and shoulder at 230 nm, acid and base stable, slightly heat labile over 80° C., and positively charged with activity on specific plant pathogens, but with no activity on bacteria. This invention further provides a process for producing this metabolite, the method comprising culturing a strain of this invention and isolating the active metabolite using the methods described below.

Further provided by this invention are compositions comprising any of the above strains (including mutants or variants thereof), supernatants, and metabolites, alone or in combination with each other, and a carrier. These compositions may be further supplemented by the addition of at least one chemical or biological pesticide. These compositions may take the form of various formulations, which include, but are not limited to, a wettable powder, a granule formulation, an aqueous suspension, an emulsifiable concentrate or microencapsulation.

In order to achieve good dispersion and adhesion of compositions within the present invention, it may be advantageous to formulate the whole broth culture, supernatant and/or metabolite/antibiotic with components that aid dispersion and adhesion. Accordingly, suitable formulations will be known to those skilled in the art (wettable powders, granules and the like, or can be microencapsulated in a suitable medium and the like, liquids such as aqueous flowables and aqueous suspensions, and emulsifiable concentrates). Other suitable formulations will be known to those skilled in the art.

Any of the above noted strains, metabolites, supernatants and compositions containing these active ingredients, may be used to provide a method of treating or protecting plants, roots or fruit from fungal infections. The method comprises applying an effective amount of a strain, metabolite, supernatant or compositions containing these active ingredients, alone or in combination with each other and/or another biologic or chemical pesticide, to the infected root, plant or fruit. Effective amounts of these compositons also can be applied to a plant, root or fruit to prevent such infestations.

In further aspect, the invention encompasses a method of treating or protecting plants, roots or fruit from fungal diseases comprising applying an effective amount of the antibiotic produced by a strain having all the identifying characteristics of the novel strain Bacillus sp. NRRL No. B-30087. In one embodiment, the strain is Bacillus sp. NRRL No. B-30087.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The following examples are intended to illustrate, but not limit the invention.

EXAMPLES

Example 1
Characterization of Strain NRRL No. B-30087.

NRRL No. B-30087 was identified based on whole-cell cellular fatty acids, derivatized to methyl esters—FAMEs (Miller, L. T. (1982) "Single derivatization method for routine analysis of bacterial whole cell wall fatty acid methyl esters, including hydroxy acids" *J. Clin. Microbiol.* 16:584–586) and analyzed by gas chromatography using the MIDI system (Microbial Identification System, Inc., Newark, Del.). The procedure and protocols used for growing the bacterial cultures and instrument specification are described by MIDI (identification of bacteria by gas chromatography of cellular fatty acids. Technical Note #101. MIDI, Inc., 115 Barksdale Professional Center, Newark, Del.). Isolates were grown on TSA (BBL) plates at 28° C. for 24 hours and cells harvested. One ml of a methanolic NaOH (15% [wt/vol] NaOH in 50% [vol/vol] methanol) was added and cells were saponified at 100° C. for 30 minutes. Esterification of fatty acids was performed with 2 mls of 3.25 N HCl in 46% (vol/vol) methanol at 80° C. for 10 minutes. The FAMEs were extracted into 1.25 ml of 1:1 (vol/vol) methyl-tert-butyl ether-hexane, and the organic extract washed with 3 ml of 1.2% (wt/vol) NaOH before analysis by gas chromatography. The gas chromatograph (Hewlett-Packard 5890A) was equipped with a flame ionization detector and capillary column (Hewlett-Packard 19091B-102, Cross-linked 5% phenyl-methyl silicone; 25 m×0.22 mm ID; film thickness, 0.33 μm; phase ratio of 150) with hydrogen as the carrier gas. FAME peaks were automatically integrated by a Hewlett-Packard 3392 integrator and bacterial isolates named using the MIDI Microbial Identification Software (Sherlock TSBA Library version 3.80). The FAME profile of Xanthomonas maltophila ATCC 13637 was used as reference check for the MIDI determinations.

The results of the three separate runs of the MIDI profile identified NRRL No. B-30087 as a *Bacillus pumilus* with a similarity index score of 0.875.

EXAMPLE 2
Activity of NRRL No. B-30087 against plant pathogens in in vitro culture (zone assay).

To determine if NRRL No. B-30087 is effective against a wide range of plant pathogenic fungi, the following experiment was performed using these plant pathogens: *Botrytis cinerea, Alternaria brassicicola Colletotrichum acutatum, Cladosporium carophylum Monilinia fructicola, Venturia inaequalis, Rhizoctonia solani, Sclerotinia sclerotiorum, Fusarium oxysporum, Taphrina deformans,* and *Verticillium dahliae.*

To determine the activity of NRRL No. B-30087 in an agar diffusion (zone) assay, plant pathogen spores (spores were scraped from the surface of petri plates and diluted to approximately 1×10⁵ spores/ml (depending on the pathogen) were spread onto the agar were spread over the surface of potato dextrose agar in 10 cm petri dishes. For *Rhizoctonia solani* and *Sclerotinia sclerotiorum*, mycelial fragments instead of spores were spread onto the plates. Circular wells, approximately 7.0 mm were removed from the agar and a 125 μL sample of the supernatant of NRRL No. B-30087 grown in a soy, yeast extract medium in 250 ml shake flasks for 72 hours was placed in the well. Supernatant was prepared by centrifuging at 12,000 rpm for 10 minutes. Typical results can consist of a zone of no growth and/or reduced growth of the pathogen around the well or no zone at all. The zone size in millimeters was measured and recorded if there was a zone. The results are shown in Table 1.

TABLE 1

Results of in vitro zone tests of NRRL No. B-30087 against fungal plant pathogens

| | |
|---|---|
| Alternaria brassicicola | No Zone |
| Botrytis cinerea | No Zone |
| Cladosporium carpohilum | No Zone |
| Colletotrichum acutatum | No Zone |
| Fusarium oxysporum | No Zone |
| Monilinia fructicola | No Zone |
| Rhizoctonia solani | No Zone |
| Sclerotinia sclerotiorum | No Zone |
| Taphrina deformans | No Zone |
| Venturia inaequalis | No Zone |
| Verticillium dahliae | No Zone |
| Pythium sp. | No Zone |
| Phytophthora infestans | Weak activity (small, hazy zone) |
| Phytophthora capsici | No Zone |
| Didimella bryonia | No Zone |

NRRL No. B-30087 supernatant showed no activity against most fungal plant pathogens in zone tests.

EXAMPLE 3
Activity of NRRL No. B-30087 against bacterial plant pathogens.

A standard agar diffusion assay was set up as in example 2. A lawn of each bacterial pathogen was spread over the surface of potato dextrose agar. A 125 μL sample of NRRL No. B-30087 supernatant was placed in each well as described previously. The presence of a zone or size of the zone was measured in millimeters.

TABLE 2

| In-Vitro Inhibition of Bacterial Plant Pathogens (Zone Test) | |
|---|---|
| NRRL No. B-30087 Supernatant: | Inhibition Zone (mm) |
| Pseudomonas syringae pv. tomato | No Zone |
| Xanthomonas campestris pv. campestris | No Zone |
| Erwinia carotovora subsp. carotovora | No Zone |

NRRL No. B-30087 was not active against any species of bacterial plant pathogens tested in vitro.

EXAMPLE 4
Activity of NRRL No. B-30087 against plant pathogens in plant tests.

The activity of NRRL No. B-30087 was tested against bean rust, *Uromyces phaseoli* on snap bean, and gray mold, *Botrytis cinerea* on pepper plants, *Alternaria solani* on tomato plants, and downy mildew of lettuce, *Bremia lactucae*; downy mildew of Brassica, *Peronospora parasitica*, late blight of tomato, *Phytophthora infestans*, and grape powdery mildew, *Uncinula necator.*

Alternaria solani

The pathogen, *Alternaria solani*, was grown on standard petri plate (10 cm) with PDA. Fungal colonies are cut from the plate and placed on sporulation medium (20 g sucrose, 30 g calcium carbonate, and 20 g agar per liter of sterile water). Sterile water is added to the plate to partially cover the mycelial blocks and plates are incubated at 22–26° C. with a 14 hour photoperiod for two days. Spores are harvested by scraping the mycelial blocks into a beaker of sterile water. The spore suspension is adjusted to $2 \times 10^4$ spores/ml).

Tomato seedlings (UC82-B) at the 3–4 leaf stage planted in two inch pots and placed in flats, were sprayed with an artists air brush to runoff with NRRL No. B-30087 whole broth grown in a soy flour, yeast extract medium for 72 hours in 250 ml shake flasks. After spraying, the seedlings were allowed to dry a minimum of two hours. Inoculated seedlings were placed in a Percival dew chamber at 22° C. with no illumination for the first 40 hours. The plants in each flat were covered with a plastic dome and kept at 20–22° C. for 48 hours in the Percival incubator at a 14 hour photoperiod. Water with no NRRL No. B-30087, with and without spores of the pathogen was used as a negative control and a positive pathogen control. Also, a chemical fungicide (e.g., Azoxystrobin, Abound®) was used for comparison at rates from 100 to 250 ppm. The plants were scored on a scale from 0 to 5, where 5 is 100% infected and 0 has no symptoms present. On the water *A. solani* control, there were uniform lesions over all the leaves and the cotyledons were detached and severely infected (rating of 5=complete infection, no control). NRRL No. B-30087 treated plants looked no different from the water control—there was no control of the pathogen by NRRL No. B-30087 (also a rating of 5). The negative control was not infected. The chemically treated plants had a score between 0 and 1.

*Botrytis cinerea*

The pathogen, *Botrytis cinerea*, was grown on standard petri plate (10 cm) with PDA and spores were collected using potato dextrose broth (PDB) supplemented with malt (0.5 g/L) and yeast extract (0.5 g/L) and adjusted to $1\times10^6$ spores/ml. The plants used were peppers (Yolo Wonder) grown in two inch pots to the 3–5 true leaf stage. The application of NRRL No. B-30087 and the pathogen were the same as above. Flats with pots were incubated at a constant 20° C. with no illumination. They were covered with plastic domes and left for 2.5 days (60 to 65 hours) until scoring.

A chemical fungicide (e.g., Iprodione, Rovral®) was used for comparison at rates from 20 to 100 ppm. The plants were scored on a scale from 0 to 5, where 5 is 100% infected and 0 has no symptoms present. On the water *B. cinerea* control, there were uniform lesions over all the leaves (rating of 5=complete infection, no control). NRRL No. B-30087 treated plants looked no different from the water control—there was no control of the pathogen by NRRL No. B-30087 (also a rating of 5). The negative control was not infected. The chemically treated plants had a score between 0 and 1.

*Bremia lactucae*

For the Bremia test, lettuce seeds were planted in a layer of sterilized potting mix containing peat, perlite and vermiculite in small clear plastic plant boxes measuring about 8 centimeters high and square. One week after planting, the lettuce seedlings were sprayed with the NRRL No. B-30087 broth or supernatant sample. The plants were allowed to dry and then a downy mildew spore suspension collected from infected lettuce seedlings ($2\times10^4$ spores/ml) was sprayed onto the seedlings. Chemical standards consisting of Aliette (fosetyl-al) and Ridomil (metalaxyl) were also applied. However, the isolate of *Bremia lactucae* used in these tests was previously demonstrated to be insensitive to these two chemical standards that are used commercially. The plastic boxes were covered with tight fitting lids and incubated at 15–16° C. in a Percival incubator for 16 hours without illumination. Plastic boxes were then placed at room temperature (20–26° C.) under lights for six days. Seedlings were uncovered, sprayed with water, recovered, and returned to the incubator at 15-16° C. for sporulation to occur overnight. The effect of NRRL No. B-30087 against a chemically-resistant strain of lettuce downy mildew is shown below:

| | Score | | |
|---|---|---|---|
| | Rep 1 | Rep 2 | Rep 3 |
| NRRL No. B-30087 Sample 1 | 0.0 | 1.0 | 1.0 |
| NRRL No. B-30087 Sample 2 | 1.0 | 1.0 | 0.0 |
| Aliette 240 ppm | 5.0 | 3.0 | — |
| Ridomil 125 ppm | 3.0 | 3.0 | — |
| Water check | 5.0 | 5.0 | 5.0 |

NRRL No. B-30087 had excellent activity against lettuce downy mildew with little to none sporulation of the pathogen on the seedlings, whereas the control (check) plants were completely sporulated with downy mildew. The chemical standards did not effectively control the pathogen.

*Peronospora parasitica*

Bacillus strain NRRL No. B-30087 was grown as above in 250 ml shake flasks. The whole broth culture at 1× strength was sprayed onto one week-old cauliflower or brussel sprout plants at the full cotyledon stage with an artist's air brush powered by compressed air. Three replicates of 15–25 seedlings/pot were sprayed per treatment. A spore suspension of downy mildew, *Peronospora parasitica* at $1–5\times10^4$ spores/ml was sprayed onto the Brassica plants after first applying the NRRL No. B-30087. Chemical standards consisting of Aliette (fosetyl-al) and Ridomil (metalaxyl) were also applied. However, the isolate of *Peronospora parasitica* used in these tests was previously demonstrated to be insensitive to these two chemical standards that are used commercially. The plants were held at 15–17° C. for 16 hours for infection, then the seedlings were incubated at 20–24° C. for six days. The pots were returned to 15–17° C. overnight for sporulation of the pathogen to occur. Each plant was evaluated by estimating the percent disease control based on a scale from 0 to 5. A zero rating is a plant with no sporulating lesions. The results averaged across replicate pots are shown below:

| | Score | | |
|---|---|---|---|
| | Rep 1 | Rep 2 | Rep 3 |
| NRRL No. B-30087 Sample 1 | 0.5 | 1.0 | 0.5 |
| NRRL No. B-30087 Sample 2 | 0.5 | 0.5 | 1.0 |
| Aliette 240 ppm | 5.0 | 3.0 | — |
| Ridomil 125 ppm | 4.0 | 4.0 | 4.0 |
| Water check | 5.0 | 3.0 | 5.0 |

The NRRL NO. B-30087 controlled the Brassica downy mildew effectively compared to the untreated check and the chemical standards.

*Uncinula necator*

Grape seedlings (Chardonnay) were grown in two inch pots until the 6–9 true leaf stage. The culture of powdery mildew was maintained on grape seedlings at 22–26° C. under a 14 hour photoperiod. All but the youngest 2–4 leaves are removed. The NRRL No. B-30087, the chemical fungicide (Rally®, myclobutanil at 25 ppm) and the water check are applied to runoff as above for the other pathogens tested.

Four to five replications are used for each treatment. To inoculate with powdery mildew, leaves with mildew on maintenance seedlings are removed with scissors and each plant is inoculated individually. The surface of the maintenance seedling is gently brushed with a paintbrush so that spores are deposited onto the upper surface of the test plants. The procedure is performed using a 3× lighted magnification lens to assure all plants are getting equivalent inoculum. Flats with pots are placed in the dark for 16–24 hours at 20–24° C. Flats are kept at 22–26° C. with a 14 hour photoperiod for an additional 9–11 days until the test is read. As above, the plants are given a score of 0 to 5.
The results with NRRL No. B-30087 are below:

|  | Score | | | |
| --- | --- | --- | --- | --- |
|  | Rep 1 | Rep 2 | Rep 3 | Rep 4 |
| NRRL No. B-30087 | 0.5 | 0 | 1 | 1 |
| Rally 25 ppm | 0 | 0 | 0 | 0 |
| Water check | 4.0 | 5.0 | 3.0 | 4.0 |

NRRL No. B-30087 controlled the Uncinula powdery mildew effectively compared to the untreated check and almost as well as the chemical standard, Rally.

*Phytophthora infestans*

The test of tomato late blight, *P. infestans* was conducted as using tomato seedlings (UC82-B) at the 4–6 true leaf stage grown in two-inch square plastic pots. Applications of NRRL No. B-30087 grown as previously described were made to the tomato seedlings. Inoculum of *P. infestans* was produced by scraping a sporulating colony grown on rye seed agar and adjusting the inoculum concentration to between 0.7 to $1.0 \times 10^4$ sporangia/ml. Inoculated seedlings were placed into flats and incubated exactly as described for the *A. solani* test. Seedlings were evaluated on a 0–5 scale. Quadris® (azoxystrobin) was used for comparison at a rate of 62.5 to 125 ppm. The results with NRRL No. B-30087 are below:

|  | Score | | | | |
| --- | --- | --- | --- | --- | --- |
|  | Rep 1 | Rep 2 | Rep 3 | Rep 4 | Rep 5 |
| NRRL No. B-30087 | 2.0 | 1.5 | 1.5 | 0.5 | 2 |
| Quadris 125 ppm | 0 | 0 | 0 | 0 | 0 |
| Quadris 62.5 ppm | 0 | 0.5 | 0 | 0.5 | 0 |
| Water check | 5.0 | 5.0 | 4.0 | 4.0 | 5.0 |

NRRL No. B-30087 controlled late blight nearly as well as the chemical standard, Quadris after four days of incubation.

*Uromyces phaseoli*

The test of bean rust, *U. phaseoli* was conducted using snap bean seedlings (Provider variety) until the first primary leaves were ¾ expanded. Applications of NRRL No. B-30087 were made as previously described for the other host/pathogen combinations. Inoculum of the rust pathogen was stored as dried rust spores in vials at −20° C. Inoculum was prepared by adding dried rust spores to water with 0.01% Tween 20 and stirred vigorously on a magnetic stirrer for at least one hour. Inoculum is adjusted to $2-4 \times 10^5$ spores/ml. The primary leaves are inoculated and seedlings are placed in flats and incubated overnight at 20° C. in a Percival dew chamber. Seedlings are then incubated at room temperature (20–26° C.) for an additional 8–10 days. Seedlings are rated on a 0 to 5 scale based on the incidence and severity of sporulating rust pustules present. The chemical fungicide, Break® (propiconazole) was used for comparison at a rate of 40 ppm. The results with NRRL No. B-30087 whole broth are below:

|  | Score | | |
| --- | --- | --- | --- |
|  | Rep 1 | Rep 2 | Rep 3 |
| NRRL No. B-30087 | 0.5 | 0.5 | 0 |
| Break 40 ppm | 0 | 0 | 0.5 |
| Water check | 5.0 | 5.0 | 5.0 |

NRRL No. B-30087 controlled bean rust as well as the chemical standard, Break.

EXAMPLE 5

Antifingal metabolite produced by NRRL No. B-30087.

The whole broth of NRRL No. B-30087 was partitioned into ethyl acetate, butanol and aqueous fractions. Each fraction was tested against snapdragon rust in a spore germination assay. Snapdragon rust spores were germinated in the presence of each sample in a depression microscope slides containing 40 μL of sample and 20 μl of pathogen spores. Approximately 16 hours later the spores are observed under a microscope to see if they have germinated. No germination (score of 0) compared to the water control (100% germination and growth=score of 5) indicates activity of the sample being tested. Results of the rust germination assay with different NRRL No. B-30087 fractions are shown below (score on a 0 to 5 rating as above):

|  | Score | | |
| --- | --- | --- | --- |
|  | Rep 1 | Rep 2 | Rep 3 |
| Ethyl acetate | 5 | 2 | 3 |
| n-butanol | 3 | 5 | 3 |
| Aqueous | 0 | 0 | 0 |
| Whole broth | 0 | 0 | 0 |
| Water Check | 4 | 5 | 5 |

The metabolite is clearly in the water soluble fraction and is not readily extractable in butanol or ethyl acetate.

Other characteristics of the metabolite were determined. The molecule was shown to pass through a 10,000 molecular weight cut off filter indicating the metabolite is smaller than 10,000 Dalton. The activity was not lost after treatment with proteases nor when treated with acid or base. The activity was slightly lost upon heating to 80° C. for one hour (the score against snapdragon rust increased from 0 to 1.5). The activity was absorbed on cation resin, but not on anion resin (the metabolite is positively charged).

It is to be understood that while the invention has been described in conjunction with the above embodiments, that the foregoing description and the examples are intended to illustrate and not limit the scope of the invention. Other aspects, advantages and modifications within the scope of the invention will be apparent to those skilled in the art to which the invention pertains.

What is claimed is:

1. A biologically pure culture of a strain having all the identifying characteristics of a *Bacillus pumilus* strain designated NRRL No. B-30087, or mutants thereof, that have fungicidal activity.

2. A biologically pure culture of a *Bacillus pumilus* strain designated NRRL No. B-30087.

3. A composition comprising the biologically pure culture of claim 1 and a carrier.

4. The composition of claim 3, wherein the composition is formulated from the group consisting of a wettable powder, a granule, an aqueous suspension, an emulsifiable concentrate and a microencapsulated formulation.

* * * * *